(12) United States Patent
Malnou

(10) Patent No.: US 8,883,126 B2
(45) Date of Patent: Nov. 11, 2014

(54) WATER-BASED NAIL-POLISH COMPOSITION

(75) Inventor: Alain Malnou, Routout (FR)

(73) Assignee: Fiabila, Maintenon (FR)

( * ) Notice: Subject to any disclaimer, the term of this patent is extended or adjusted under 35 U.S.C. 154(b) by 1255 days.

(21) Appl. No.: 11/919,483

(22) PCT Filed: Apr. 21, 2006

(86) PCT No.: PCT/FR2006/000893
§ 371 (c)(1),
(2), (4) Date: Dec. 14, 2007

(87) PCT Pub. No.: WO2006/117449
PCT Pub. Date: Nov. 9, 2006

(65) Prior Publication Data
US 2009/0068131 A1    Mar. 12, 2009

(30) Foreign Application Priority Data

Apr. 29, 2005 (FR) ..................................... 05 04376

(51) Int. Cl.
*A61K 8/04* (2006.01)
*A61K 8/06* (2006.01)
*A61K 8/18* (2006.01)
*A61K 8/81* (2006.01)
*A61Q 3/02* (2006.01)
*B82Y 5/00* (2011.01)

(52) U.S. Cl.
CPC ................ *A61Q 3/02* (2013.01); *A61K 8/8152* (2013.01); *A61K 8/044* (2013.01); *A61K 2800/413* (2013.01); *A61K 8/8147* (2013.01); *B82Y 5/00* (2013.01)
USPC ........................................................ 424/61

(58) Field of Classification Search
None
See application file for complete search history.

(56) References Cited

U.S. PATENT DOCUMENTS

| 5,817,304 A | 10/1998 | Mondet et al. | |
| 5,922,334 A * | 7/1999 | Krasnansky et al. | 424/401 |
| 6,139,822 A * | 10/2000 | Socci et al. | 424/61 |
| 6,524,598 B2 * | 2/2003 | Sunkel et al. | 424/401 |
| 2003/0228424 A1 * | 12/2003 | Dove et al. | 427/553 |
| 2004/0170584 A1 * | 9/2004 | Renard | 424/61 |
| 2005/0159536 A1 * | 7/2005 | Smith | 524/501 |

FOREIGN PATENT DOCUMENTS

| EP | 0 752 244 A1 | 1/1997 |
| EP | 1 371 685 A2 | 12/2003 |
| EP | 1 371 693 A2 | 12/2003 |
| FR | 2 733 147 A | 10/1996 |
| JP | 4-103513 A | 4/1992 |
| JP | 04-297408 | 10/1992 |
| JP | 6-298624 A | 10/1994 |

OTHER PUBLICATIONS http://www.dispersions-pigments.basf.us/p02/USWeb-Internet/pigments/en_GB/function/conversions:/publish/content/microsites/pigmentsdispersions/Brochures/2010_BASF_CO_SelGuide_EL.pdf: BASF Resins Industrial Coatings Selection Guide, accessed on Jan. 3, 2012.*
Japanese Office Action, dated Sep. 27, 2011, in Application No. 2008-508254.

* cited by examiner

*Primary Examiner* — David J Blanchard
*Assistant Examiner* — Tigabu Kassa
(74) *Attorney, Agent, or Firm* — Young & Thompson

(57) ABSTRACT

The water-based nail-polish composition includes a mixture of at least one water-based suspension (A) of hard nanoparticles of an acrylic polymer at a glass transition temperature that is greater than or equal to 55° C., in combination with at least one coalescent and/or plasticizing solvent of the polymer; and at least one water-based suspension (B) of nanoparticles of acrylic monomers, partially cross-linked, that have a film formation temperature of less than 15° C. The water-based composition can also contain a solution (C) of an acrylic polymer of low molecular weight that is less than approximately 20,000, with a high acid value, neutralized to a pH of between 7 and 8.5, approximately.

11 Claims, No Drawings

WATER-BASED NAIL-POLISH COMPOSITION

This invention relates to a nail-polish composition, in particular a water-based composition.

The traditional nail polishes, based on nitrocellulose resins, contain large proportions of organic solvents. As a result, these polishes are inflammable with some risks of toxicity.

As for paints, the formulators sought to develop water-based polishes. For this purpose, it is necessary to solve the three primary problems that include the speed of drying and hardening of the film, the brilliance of the film that is obtained, and the adherence of this film to the nail.

The most frequently proposed solutions are based on the use of dispersions or suspensions of polymers in water, preferably suspensions of acrylic copolymers, vinyl copolymers, polyesters, polyurethanes, etc.

To form a cohesive film, the particles of these suspensions have to coalesce, with or without the assistance of coalescents and/or plasticizers. The coalescent solvents evaporate during drying; the plasticizing solvents remain primarily in the film.

To solve these problems, the authors tested the use of suspensions of various polymers, of different sizes and mixtures thereof, of suspensions of different hardnesses (glass transition temperatures) that are coalesced and/or plasticized by solvents of different natures, having different boiling points, of suspensions of different compositions (acrylic, vinyl, polyurethane) or that use particular monomers.

The applicant found that a water-based composition that has acceptable properties for use in nail polish could be obtained from a mixture of polymers with particular characteristics.

The water-based nail-polish composition according to this invention is therefore characterized in that it comprises a mixture of

- At least one water-based suspension (A) of hard nanoparticles of an acrylic polymer at a glass transition temperature that is greater than or equal to 55° C., preferably greater than 60° C., in combination with at least one coalescent and/or plasticizing solvent of said polymer;
- And at least one water-based suspension (B) of nanoparticles of acrylic, pre-crosslinked monomers that have a film formation temperature of less than 15° C.

The water-based nail-polish composition according to the invention can also contain a solution (C) of an acrylic polymer of low molecular weight of less than approximately 20,000, with a high acid value, neutralized at a pH of between approximately 7 and 8.5.

The nanoparticles of the suspension (A) are preferably based on a polymer with a molecular weight of more than approximately 200,000 and have a size of approximately 40 to 80 nanometers.

The water-based suspension (A) is plasticized in advance, in particular by a coalescent solvent and/or a plasticizer of the polymer of this suspension. Actually, to be able to form a film, this suspension (A) has to be "softened" with one or more predefined solvents for lowering the film formation temperature. These solvents do not destabilize the suspension and are stable in water. After the formation of the film, the coalescent solvent of the polymer of the suspension will evaporate during drying and will restore to the film the initial hardness of the suspension. Unlike the so-called coalescent solvent, the plasticizer remains in the film and participates in the hardness/flexibility compromise of the final film.

Advantageously, the coalescent is a glycol ether that is selected from among propylene glycol n-butyl ether, dipropylene glycol methyl ether, dipropylene glycol dimethyl ether, tripropylene glycol methyl ether or a mixture of the latter, and the plasticizer is selected from among an alkyldiol butyrate (such as trimethyl-pentanediol monoisobutyrate), dibutyl adipate, dibutyl sebacate, tributyl acetyl citrate, triethyl citrate or a mixture of the latter.

The coalescent and/or plasticizing solvents are each used in proportions of up to 15%, preferably between 5 and 15%, by weight relative to the polymer of the suspension (A).

The suspension (A) that is used for this invention preferably has a low acid value (but advantageously more than about 60 milligrams of KOH per gram of polymer), and it is neutralized by ammonia.

Advantageously, the nanoparticles of the suspension (B) have a cross-linking level of between 0.5 and 5%, and a size of approximately 50 to 80 nanometers. Cross-linking rate is defined as the level of diacrylate monomers, for example, that are present in this suspension. Such a suspension provides advantageous results in terms of rapidity of drying, because the presence of di- or trifunctional monomers makes it possible to create a three-dimensional network quickly, by promoting polymerization.

The acrylic monomers and polymers of the suspensions and solutions that are described above are preferably based on styrene, methyl styrene, methyl acrylate, methyl methacrylate, butyl acrylate, butyl methacrylate, hydroxyethyl methacrylate, hydroxypropyl methacrylate or a mixture of the latter.

Preferably, the suspension (A) is rich in methyl acrylate or methyl methacrylate. The suspensions contain at least 40% monomer or polymer solids.

The solution (C) of the mixture for a water-based composition of this invention contains an acrylic polymer of low molecular weight; low molecular weight is defined as a molar mass that is less than approximately 20,000. The preferred molar mass is between 9,000 and 18,000. This water-based solution has a high acid value, i.e., more than 200 milligrams of KOH per gram of polymer, preferably 200 to 250 milligrams of KOH per gram. This solution is neutralized using a strong base up to a pH of between 7 and 8.5. The strong base is advantageously volatile and can be, for example, ammonia. Once neutralized, the acid-rich acrylic polymer becomes soluble in water, while with drying, the ammonia evaporates and the film becomes water-resistant again. The two acrylic suspensions are obtained by direct polymerization in the water, without surfactant, of the mixture of different above-mentioned monomers.

The water-based nail-polish composition according to the invention advantageously contains between 12 and 24% by weight of nanoparticles of the suspension (A), between 8 and 16% by weight of nanoparticles of suspension (B), and between 0.2 and 1% by weight of dry polymer of the optional solution (C).

If the amount of nanoparticles of (A) is less than 12% by weight, the dried polish softens over time; if it is more than 24%, the hardening is long and the removal of the polish is difficult.

For an amount of nanoparticles of (B) that is less than 8% by weight, the polish takes a long time to dry, and for an amount that is more than 16% by weight, the dried film is less cohesive and has a tendency to soften over time.

The solution (C) can be omitted when a colorless polish is prepared, although it improves the adherence and the formation of the film by its coalescent action. When it is used, it is preferable not to exceed 1% by weight that is expressed in dry polymer: acting as a water-based solution, it takes longer to dry and is sensitive to water. It is very useful when colored polishes are prepared, because it has good pigment dispersion properties.

In addition to the suspensions (A) and (B) and the solution (C), the water-based composition according to the invention can also contain water-soluble dyes and/or pigments that are dispersed in the acrylic water-based solution (C).

The composition can also contain mineral or organic thickening agents, anti-foam agents that may or may not contain silicone, preservatives, spreading and/or sliding agents, perfumes, neutralizing agents, or active additives for nail care.

The dispersions that are produced with conventional pigments that are allowed in cosmetics are stable dispersions without sedimentation or phase shift.

The nail polishes that are produced from these compositions have a drying time on the same order as a polish with solvents, characteristics of hardening within three hours, very good shine and proper hold on the nail for three days. This good hold is the result of a good hardness/flexibility compromise, good adherence and good resistance of the film to water. The polish can be easily removed with a conventional solvent based on ketones and acetates.

The following examples make it possible to illustrate this invention in a nonlimiting manner. The components of the different polish compositions tested are grouped in Table 1 (expressed in terms of weight of the final composition).

In the examples below, the suspension (A) is first plasticized with the coalescent and/or the plasticizer before being mixed with the other components of the nail polish formula. Preferably, the pigments are dispersed in the water-based acrylic solution (C) by means of a micro-ball mill.

The demineralized water is used for the suspensions (A) and (B), the solution (C), the different variations of thickening dispersions and pigments, and the final development of viscosity in the compositions.

The Joncryl components are marketed by the Johnson Polymer B.V. Company:
The Joncryl 538 is a water-based suspension of acid polymers and (meth)acrylic esters/styrene that has a film formation temperature (TMF) of 60° C. and a glass transition temperature (Tg) of 64° C.
The Joncryl 8224 is an acrylic suspension that has a TMF of 10° C. and a Tg that is close to 46° C.
The Joncryl HPD71E is a water-based solution of an ammonium salt of styrene polymers/acids and (meth) acrylic esters.

Examples 1, 3 and 4 are colored nail polishes according to the invention, designed to be applied directly to the nail in two successive layers.

Example 2 is a nail-care polish (containing Vitamin E) that is designed to be used as a base layer under a conventional polish that contains solvents.

The suspensions (A) of the compositions of Examples 1, 2 and 3 are mixed with a coalescent and a plasticizer.

The suspension (A) of the composition of Example 4 is mixed without a coalescent, i.e., the final polish does not have a volatile organic compound.

Examples 5 and 6 are comparative examples.

Example 5 is a composition of the prior art that does not contain pre-cross-linked suspension but a non-cross-linked conventional suspension Joncryl SCX 1537 of the same Tg (glass transition temperature) (here Tg=46° C.) for the purpose of having an equivalent film hardness.

Example 6 is an example of a polish without suspension (A), but with only a cross-linked suspension (B) in the presence of a type (C) solution for the dispersion of pigments, and a little coalescent for solubilizing the additives.

Different tests have been carried out from these compositions:

The viscosities are measured with a Brookfield viscosimeter with the needle No 3 at 25° C. at 6 rpm and at 60 rpm.

The stability is assessed after one month at 50° C.

The applications are made with an applicator of 100 micrometers of liquid on glass for measuring hardness and on a "Leneta"-type card for measuring the drying time.

The drying is measured by the trace left by a ball sliding on the polish applied to a "Leneta" card left on the heating plate at 35° C.

The hardness is measured using a "Persoz" pendulum on a film that is applied to a glass plate and dried for 3 hours and 24 hours at ambient temperature (20° C.).

The adherence is assessed after "clawing" of the film that is applied on the glass plate in a square grid 1 mm on a side.

The polish is then tested for hold on the nails to assess premature wear, retention of shine, chipping, and separation in water.

The different results that are obtained are summarized in Table 2.

These polishes are all stable at 50° C. for at least one month. At ambient temperature, neither sedimentation nor phase separation are noted over a long period.

The polish compositions according to the invention have good properties on the nail. In particular, they can be preserved for three days on the nail without premature wear, and with neither chipping nor separation in water. These polishes then are easily removed with conventional ester-based or ketone-based solvents.

Regarding the water-based base according to Example 2, it is applied in a single layer on the nail and can be covered by one or two layers of conventional polish with solvents. It thus makes it possible to protect the nail from the harmful effects of certain components of the solvent-based polishes, whereby the final appearance and the hold on the nail of such a system are superior to the current systems.

The viscosities and the stability are virtually equivalent from one formula to the next.

The drying depends on the rate of evaporation of the water and the coalescents. The retention of the coalescent seems less with the cross-linked suspension.

The most important result is the hardening speed that is faster in the presence of cross-linked emulsion. In addition, it was noticed that the hardness does not continue to increase over time. The film remains tough and flexible on the nail without chipping. It thus is possible to obtain a wear-resistant and abrasion-resistant film quickly on the nail, without fearing to have a film, after 24 hours, which is very hard and brittle, with chipping and loss of adherence.

This consistency of the dry film makes it possible to have good adherence to the nail. The film is not soft the first hours with wear and separation, nor hard with chipping after 24 hours. A hard and elastic film, which can be kept for several days on the nail, is obtained quickly.

The results of the adherence and the hold on the nail are directly linked to these desired hardness/flexibility properties.

The results of the Comparison Example 6 are not good because the emulsion is not hard enough to obtain the desired resistance. In addition, a film that dries very quickly but that softens on the nail over time is obtained. The presence of the suspension (A) is therefore essential.

Comparison Example 7

A formulation according to Example 1 is prepared by omitting the suspension (B). The polish that is obtained has a long hardening period due to the absence of the pre-cross-linked polymer, and it is difficult to remove.

The above-mentioned tests therefore show that the simultaneous presence of suspensions (A) and (B) is essential for obtaining the advantages that are indicated.

TABLE 1

| | Example | 1 | 2 | 3 | 4 | 5 (Comp.) | 6 (Comp.) |
|---|---|---|---|---|---|---|---|
| Suspension (A) | Joncryl 538 (with 46% Solid) | 38 | 35 | 34 | 36 | 34 | |
| Coalescent | Dipropylene Glycol Dimethyl Ether | 6 | 5 | | | | |
| Coalescent | Dipropylene Glycol Monomethyl Ether | | | 3 | / | 3 | 3 |
| Plasticizer | Trimethyl Pentanediol Monoisobutyrate | 4 | 3 | 4 | 5 | 4 | |
| Active Ingredient | Vitamin E Acetate | | 0.1 | | | | |
| Suspension (B) | Joncryl 8224 (with 45% Solid) | 35 | 45 | 45 | 44 | | 80 |
| Suspension | Not Cross-linked with Tg = 46° C. and TMF = 45° C. | | | | | 45 | |
| Thickener | Silicate of Mg and Na | 0.6 | | 0.6 | 0.6 | 0.6 | 0.6 |
| Preservative | Paraben Solution in Phenoxyethanol | 0.5 | 0.5 | 0.5 | 0.5 | 0.5 | 0.5 |
| Thickener | Organic Thickener | 0.5 | 0.8 | 0.8 | 0.8 | 0.8 | 0.8 |
| Additive | Silicone-Containing Tensor and Sliding Agent | 0.5 | | 0.5 | 0.5 | 0.5 | 0.5 |
| Solution (C) | Joncryl HPD 71 E (with 25% Solid) | 3 | | 3 | 3 | 3 | 3 |
| Pigment | DC red 34 | 0.3 | | 0.3 | 0.3 | 0.3 | 0.3 |
| Pigment | DC red 7 | 0.3 | | 0.3 | 0.3 | 0.3 | 0.3 |
| Pigment | Mica Titanium | 2 | | 2 | 2 | 2 | 2 |
| Pigment | DC red 30 | | 0.01 | | | | |
| Diluent | Demineralized Water, Made up to 100 | QS | QS | QS | QS | QS | QS |

TABLE 2

| | Example | 1 | 2 | 3 | 4 | 5 (Comp.) | 6 (Comp.) |
|---|---|---|---|---|---|---|---|
| Brookfield Viscosity (mPa · s) | Speed 6 Turns | 1620 | 860 | 1700 | 1200 | 1540 | 1485 |
| | Speed 60 Turns | 620 | 740 | 895 | 672 | 732 | 760 |
| Drying (min) | at 35° C. | 5 min 30 | 5 min 45 | 7 min 15 | 6 min 15 | 8 min | 5 min 15 155 |
| Persoz Hardness (Seconds) | After 3 Hours of Drying | 150 | 145 | 160 | 165 | 125 | 175 |
| | After 24 Hours of Drying | 210 | 190 | 198 | 191 | 175 | |
| Adherence | (0 Excellent, 5 Poor) | 0/1 | 0/1 | 0/1 | 0/1 | 1 | 1 |
| Shine | | 79 | 82 | 88 | 80 | 82 | 78 |
| Stability at 50° C. | | Ok | Ok | Ok | Ok | Ok | Ok |
| Hold on the Nail | At 3 Days | Ok | Ok | Ok | Ok | Wear | Wear |
| Appearance | | Shiny | With Polish Solvent | Shiny | Shiny | Dull | Softening |

The invention claimed is:

1. A water-based nail-polish composition, comprising a mixture of:
    a water-based suspension (A) of hard nanoparticles of a size from 40 to 80 nm of acid and (meth) acrylic esters/styrene polymers having a film formation temperature (TMF) of 60° C. and a glass transition temperature of 64° C., in combination with at least one coalescent and/or plasticizing solvent of said polymer, said polymer having a molecular weight of more than approximately 200,000, said hard nanoparticles being 46% by weight of said suspension(A), and said hard nanoparticles between 12 and 24% by weight of said water-based nail polish composition; and
    a water-based suspension (B) of nanoparticles of a size from 50 to 80 nm of acrylic, pre-cross-linked monomers that have a film formation temperature of 10° C. and a glass transition temperature of 46° C., said nanoparticles having a cross-linking level of between 0.5 and 5%, said nanoparticals being 45% by weight of said suspension (B), and said nanoparticles being between 8 and 16% by weight of said water-based nail polish composition.

2. The water-based nail polish composition according to claim 1, further comprising a solution (C) of an ammonium salt of styrene polymers/acid and (meth)acrylic esters of low molecular weight that is less than approximately 20,000, with a high acid value, neutralized to a pH of between 7 and 8.5, said ammonium salt of styrene polymers/acid and (meth)acrylic esters being 25% by weight of said solution (C), and said ammonium salt of styrene polymers/acid and (meth)acrylic esters being between 0.2 and 1% by weight of said water-based nail polish composition.

3. The water-based nail polish composition according to claim 1, wherein the coalescent solvent of the polymer of the suspension (A) is a glycol ether that is selected from the group consisting of propylene glycol n-butyl ether, dipropylene glycol methyl ether, dipropylene glycol dimethyl ether, tripropylene glycol methyl ether, and mixtures thereof.

4. The water-based nail polish composition according to claim 1, wherein the plasticizing solvent of the polymer of the suspension (A) is selected from the group consisting of dibutyl adipate, dibutyl sebacate, tributyl acetyl citrate, triethyl citrate, an alkyldiol butyrate, or a and mixtures thereof.

5. The water-based nail polish composition according to claim 1, wherein the coalescent and/or plasticizing solvents of the polymers of the suspension (A) are each used in proportions of up to 15%.

6. The water-based nail polish composition according to claim 2, further comprising water-soluble dyes and/or pigments that are dispersed in the solution (C).

7. The water-based nail polish composition according to claim 1, further comprising mineral or organic thickening agents, antifoam agents that may or may not contain silicone, preservatives, spreading and/or sliding agents, perfumes, neutralizing agents, or active additives for nail care.

8. The water-based nail polish composition according to claim 1, having the following components with corresponding percentages by weight of the composition:

| | | |
|---|---|---|
| Suspension (A) | said supsension (A) of hard nanoparticles of a size from 40 to 80 nm of acid and (meth) acrylic esters/styrene polymers having a film formation temperature (TMF) of 60° C. and a glass transition temperature of 64° C., said polymer having a molecular weight of more than approximately 200,000, said hard nanoparticles being 46% by weight of said suspension (A), and said hard nanoparticles between 12 and 24% by weight of said water-based nail polish composition | 38 |
| Coalescent Plasticizer | Dipropylene Glycol Dimethyl Ether | 6 |
| | Trimethyl Pentanediol Monoisobutyrate | 4 |
| Suspension (B) | said suspension (B) of nanoparticles of a size from 50 to 80 nm of acrylic, pre-cross-linked monomers that have a film formation temperature of 10° C. and a glass transition temperature of 46° C., said nanoparticles having a cross-linking level of between 0.5 and 5%, said nanoparticles being 45% by weight of said suspension (B), and said nanoparticles being between 8 and 16% by weight of said water-based nail polish composition | 35 |
| Mineral Thickener | Magnesium Silicate and Sodium Silicate | 0.6 |
| Preservative | Paraben Solution in the Phenoxyethanol | 0.5 |
| | Organic Thickener | 0.5 |
| | Silicone-Containing Tensor and Sliding Agent | 0.5 |
| Solution (C) | said solution (C) is a solution of an ammonium salt of styrene polymers/acid and (meth)acrylic esters of low molecular weight that is less than approximately 20,000, with a high acid value, neutralized to pH of between 7 and 8.5, said ammonium salt of styrene polymers/acid and (meth)acrylic esters being 25% by weight of said solution (C) | 3 |
| Pigments | DC Red 34 | 0.3 |
| | DC Red 7 | 0.3 |
| | Titanium Mica | 2 |
| Water | Demineralized Water Made up to 100. | |

9. The water-based nail polish composition according to claim 1, having the following components with corresponding percentages by weight of the composition:

| | | |
|---|---|---|
| Suspension (A) | said supsension (A) of hard nanoparticles of a size from 40 to 80 nm of acid and (meth) acrylic esters/styrene polymers having a film formation temperature (TMF) of 60° C. and a glass transition temperature of 64° C., said polymer having a molecular weight of more than approximately 200,000, said hard nanoparticles being 46% by weight of said suspension (A), and said hard nanoparticles between 12 and 24% by weight of said water-based nail polish composition | 35 |
| Coalescent Plasticizer | Dipropylene Glycol Dimethyl Ether | 5 |
| | Trimethyl Pentanediol Monoisobutyrate | 3 |
| | Vitamin E Acetate | 0.1 |
| Suspension (B) | said suspension (B) of nanoparticles of a size from 50 to 80 nm of acrylic, pre-cross-linked monomers that have a film formation temperature of 10° C. and a glass transition temperature of 46° C., said nanoparticles having a cross-linking level of between 0.5 and 5%, said nanoparticles being 45% by weight of said suspension (B), and said nanoparticles being between 8 and 16% by weight of said water-based nail polish composition | 45 |
| Preservative | Paraben Solution in Phenoxyethanol | 0.5 |
| | Organic Thickener | 0.8 |
| Solution (C) | Said solution (C) is a solution of an ammonium salt of styrene polymers/acid and (meth)acrylic esters of low molecular weight that is less than approximately 20,000, with a high acid value, neutralized to pH of between 7 and 8.5, said ammonium salt of styrene polymers/acid and (meth)acrylic esters being 25% by weight of said solution (C) | 3 |
| Pigments | DC Red 30 | 0.01 |
| | Demineralized Water Made up to 100. | |

10. The water-based nail polish composition according to claim 1, having the following components with corresponding percentages by weight of the composition:

| | | |
|---|---|---|
| Suspension (A) | said supsension (A) of hard nanoparticles of a size from 40 to 80 nm of acid and (meth) acrylic esters/styrene polymers having a film formation temperature (TMF) of 60° C. and a glass transition temperature of 64° C., said polymer having a molecular weight of more than approximately 200,000, said hard nanoparticles being 46% by weight of said suspension (A), and said hard nanoparticles between 12 and 24% by weight of said water-based nail polish composition | 34 |
| Coalescent Plasticizer | Dipropylene Glycol Monomethyl Ether | 3 |
| | Trimethyl Pentanediol Monoisobutyrate | 4 |
| Suspension (B) | said suspension (B) of nanoparticles of a size from 50 to 80 nm of acrylic, pre-cross-linked monomers that have a film formation temperature of 10° C. and a glass transition temperature of 46° C., said nanoparticles having a cross-linking level of between 0.5 and 5%, said nanoparticles being 45% by weight of said suspension (B), and said nanoparticles being between 8 and 16% by weight of said water-based nail polish composition | 45 |
| Mineral Thickener | Magnesium Silicate and Sodium Silicate | 0.6 |
| Preservative | Paraben Solution in Phenoxyethanol | 0.5 |
| | Organic Thickener | 0.8 |
| | Silicone-Containing Tensor and Sliding Agent | 0.5 |
| Solution (C) | said solution (C) is a solution of an ammonium salt of styrene polymers/acid and (meth)acrylic esters of low molecular weight that is less than approximately 20,000, with a high acid value, neutralized to pH of between 7 and 8.5, said ammonium salt of styrene polymers/acid and (meth)acrylic esters being 25% by weight of said solution (C) | 3 |
| Pigments | DC Red 34 | 0.3 |
| | DC Red 7 | 0.3 |
| | Titanium Mica | 2 |
| Water | Demineralized Water Made up to 100. | |

11. The water-based nail polish composition according to claim 1, having the following components with corresponding percentages by weight of the composition:

| | | |
|---|---|---|
| Suspension (A) | said supsension (A) of hard nanoparticles of a size from 40 to 80 nm of acid and (meth) acrylic esters/styrene polymers having a film formation temperature (TMF) of 60° C. and a glass transition temperature of 64° C., said polymer having a molecular weight of more than approximately 200,000, said hard nanoparticles being 46% by weight of said suspension (A), and said hard nanoparticles between 12 and 24% by weight of said water-based nail polish composition | 36 |
| Plasticizer | Trimethyl Pentanediol Monoisobutyrate | 5 |
| Suspension (B) | said suspension (B) of nanoparticles of a size from 50 to 80 nm of acrylic, pre-cross-linked monomers that have a film formation temperature of 10° C. and a glass transition temperature of 46° C., said nanoparticles having a cross-linking level of between 0.5 and 5%, said nanoparticles being 45% by weight of said suspension (B), and said nanoparticles being between 8 and 16% by weight of said water-based nail polish composition | 44 |
| Mineral Thickener | Magnesium Silicate and Sodium Silicate | 0.6 |
| | Silicone-Containing Tensor and Sliding Agent | 0.5 |
| Preservative | Paraben Solution in Phenoxyethanol | 0.5 |
| | Organic Thickener | 0.8 |
| Solution (C) | said solution (C) is a solution of an ammonium salt of styrene polymers/acid and (meth)acrylic esters of low molecular weight that is less than approximately 20,000, with a high acid value, neutralized to pH of between 7 and 8.5, said ammonium salt of styrene polymers/acid and (meth)acrylic esters being 25% by weight of said solution (C) | 3 |
| Pigments | DC Red 34 | 0.3 |
| | DC Red 7 | 0.3 |
| | Titanium Mica | 2 |
| Water | Demineralized Water Made up to 100. | |

\* \* \* \* \*